US007713234B2

(12) United States Patent
Karanzas

(10) Patent No.: US 7,713,234 B2
(45) Date of Patent: May 11, 2010

(54) SELF-INJECTION GUIDE TABLET

(76) Inventor: Doreen A. Karanzas, 58 Rock Haven Ct., Reading, PA (US) 19606

( * ) Notice: Subject to any disclaimer, the term of this patent is extended or adjusted under 35 U.S.C. 154(b) by 0 days.

(21) Appl. No.: 12/385,075

(22) Filed: Mar. 30, 2009

(65) Prior Publication Data

US 2009/0281493 A1 Nov. 12, 2009

Related U.S. Application Data

(60) Provisional application No. 61/071,625, filed on May 8, 2008.

(51) Int. Cl.
*A61M 5/00* (2006.01)

(52) U.S. Cl. ....................................................... 604/116

(58) Field of Classification Search ................. 604/116; 422/58, 99; 434/225, 262, 267, 272
See application file for complete search history.

(56) References Cited

U.S. PATENT DOCUMENTS 2,245,350 A 6/1941 Marshall
3,542,022 A 11/1970 Bartnik
3,547,121 A 12/1970 Cherry
4,228,796 A 10/1980 Gardiner
4,362,157 A 12/1982 Keeth
5,634,904 A 6/1997 Battenfield
6,319,467 B1 * 11/2001 McLernon, III .............. 422/58

* cited by examiner

*Primary Examiner*—Nicholas D Lucchesi
*Assistant Examiner*—Brooke M Matney
(74) *Attorney, Agent, or Firm*—Richard C. Litman

(57) ABSTRACT

The self-injection guide tablet for subcutaneous injections includes adhesively mounted templates with headings indicating a particular day and body injection area. Each template further includes a grid guide, designed to cover the body injection area, along with instructions for placing the grid guide on the particular body injection area. Each grid guide includes a plurality of injection grids, in column or row format, with indicia marking a predetermined injection grid. Upon removing the grid guide from the specific template, the predetermined injection grid remains on the template, so the vacated injection grid forms the injection area for the subcutaneous injection.

20 Claims, 9 Drawing Sheets

SELF-INJECTION GUIDE TABLET

CROSS-REFERENCE TO RELATED APPLICATION

This application claims the benefit of U.S. Provisional Patent Application Ser. No. 61/071,625, filed May 8, 2008.

BACKGROUND OF THE INVENTION

1. Field of the Invention

The present invention relates to medical devices, and more particularly to a self-injection guide tablet that provides a guide, template or grid applied directly to a body area for rotating subcutaneous injections for individuals who must administer such injections.

2. Description of the Related Art

Persons afflicted with diabetes and other medical conditions may receive a subcutaneous injection of medicine daily, or at some other regular interval. A subcutaneous injection, also sometimes called a "sub Q injection", is a "shot" of medicine injected into a layer between skin and muscle. Subcutaneous injections are a relatively convenient way to deliver medication that would otherwise be absorbed too slowly or be made ineffective if taken by mouth. Examples of such medicines include insulin injections for people with diabetes, epinephrine injections for people with severe allergic reactions, and administration of low molecular weight heparin (e.g., Lovenox).

It is known that only certain parts of the human body may be safely used for such self-injections without excessive discomfort or an inordinate risk of penetrating major veins or arteries. Generally, the body parts used for self-injections are on thighs, the fleshy area of the upper hips, the fleshy area of the backs of each arm, and portions of the lower abdomen. Each of these body parts has an area known as an injection area, in which a plurality subcutaneous injections may be made. However, it is also known that such injection irritates the body tissue and adjacent muscle at the point of self-injection. In fact, it may take up to two months for the skin and muscle in the injection area to heal. If another injection is made less than 5.08 centimeters, or less than two inches, to the previous injection before it is healed, a hard spot or knot will develop in the area of the injection as a result of the additional injection.

It has been found that it is difficult for the self-injection user to determine which body areas have recently received an injection because the wounds caused by the injections visibly heal quickly at the surface of the skin. Also, it is difficult to tell which body injection area has been used recently until after the second injection, because a knot develops. As a result, it is not unusual for the self-injector to make double injections and have several painful knots at any one time. Thus, a self-injection guide tablet solving the aforementioned problems is desired.

SUMMARY OF THE INVENTION

The self-injection guide tablet according to the present invention includes a template for each of the body injection areas used for self-injection. There are seven body injection areas commonly used for subcutaneous injections, including the thighs, the fleshy area of the upper hips, the fleshy area of the backs of each arm, and portions of the lower abdomen. Each of the templates has a removable guide grid with an adhesive backing in order to be peeled and mounted on one of the body injection areas used for self-injections.

To guide the individual, each of the templates is marked with indicia. The indicia define a heading that includes a day of the week and a body part for receiving the self-injection. There are also indicia defining instructions for each template for placement. Thus, the individual administering a daily subcutaneous injection has, with the self-injection guide tablet, a template indicating the particular day and body injection area for each of the seven days in a week and for the seven body injection areas.

To further provide guidance to the individual, each guide grid has a plurality of injection grids formed thereon. The injection grids each have indicia for distinguishing one grid from the other. Additionally, the injection grid receiving the injection is shaded or has other distinguishing features. To further assist the individual administering self-injections, when the guide grid is peeled from the template, the selected injection grid will remain on the template. Thus, the peeled guide grid, when placed on the specific body injection area, as instructed, will have a grid vacancy, serving as a template or guide, for receiving the injection.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
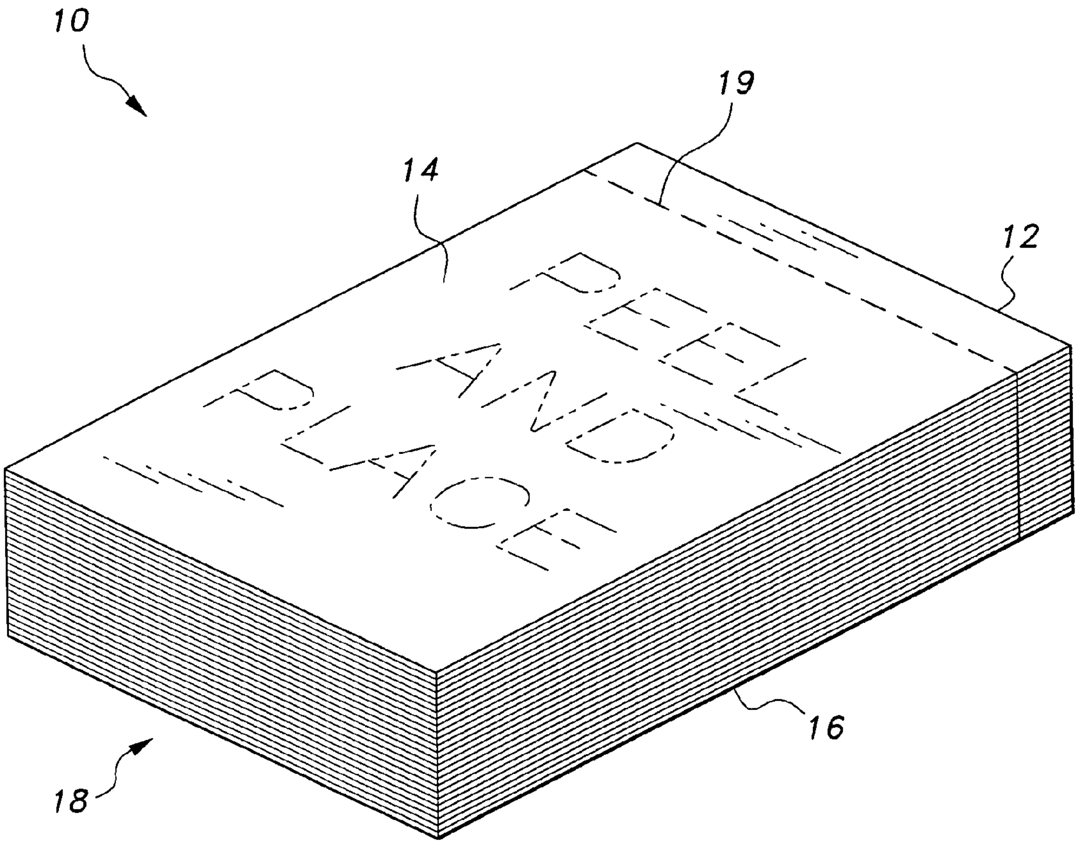
FIG. 1 is an environmental, perspective view of a self-injection guide tablet according to the present invention.

FIG. 1 shows a self-injection guide tablet, generally as 10 in the Figures. The self-injection guide tablet 10 includes a spine 12 and opposed upper and lower covers 14, 16, respectively. The upper and lower covers 14, 16 may be substantially rigid to provide support for the self-injection guide tablet 10. The spine 12 preferably has an adhesive or tape-like binding to fasten the covers 14, 16 together and to provide further support for the tablet 10. Sandwiched between the covers 14, 16 are a plurality of templates, generally indicated as 18, as will be explained in greater detail below, with specific reference to FIGS. 3-9. The templates 18 each have an adhesive backing, similar to the adhesive backing commonly found on adhesive bandages or other like materials, in order to permit easy peeling from the tablet 10 and from the self-injection areas of the body. There is also a perforation 19 extending through the tablet 10 for tearing off the templates 18.

Figure 2A:
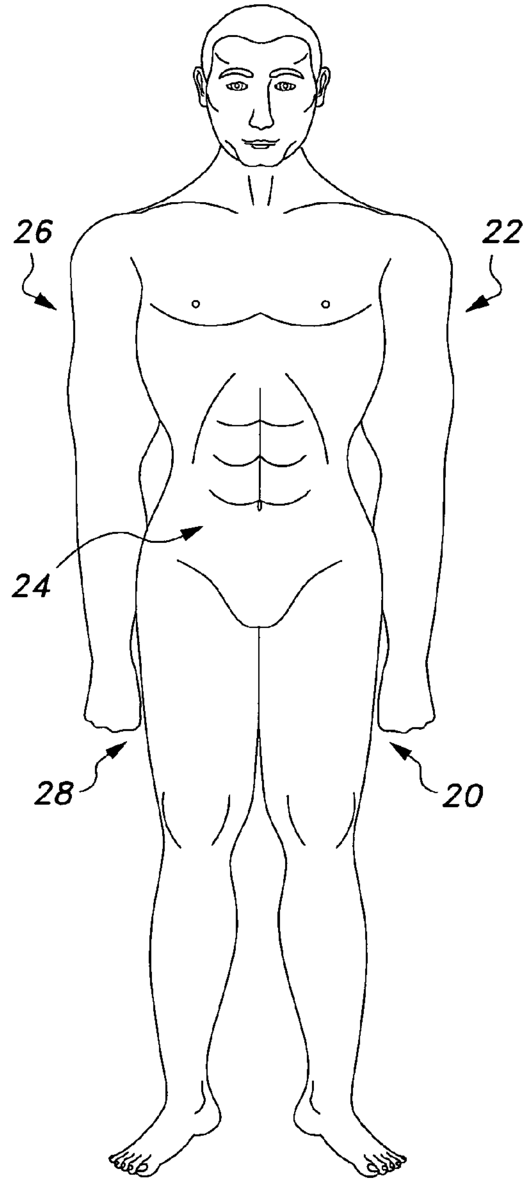
FIG. 2A and FIG. 2B illustrate body areas for known subcutaneous injections intended for use with the present self-injection guide tablet.
Figure 2B:
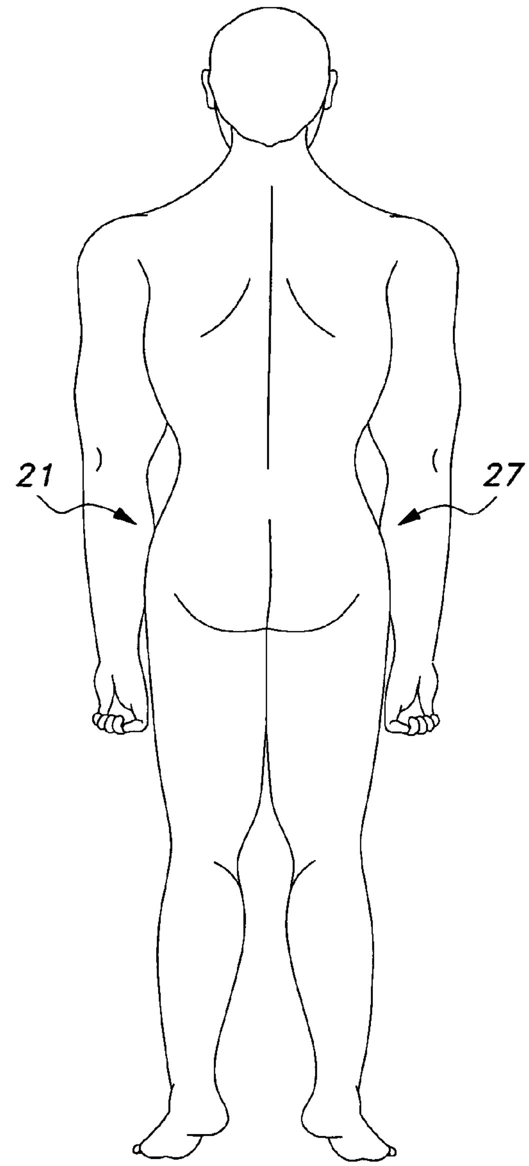

With reference to FIGS. 2A and 2B, there are indicated seven different common self-injection areas on a human body, which are typically utilized for subcutaneous injections. The injection areas are the left thigh 20, the fleshy area of the upper left hip 21, the fleshy, upper back portion of the left arm 22, the abdomen 24, the fleshy, upper back portion of the right arm 26, the fleshy area of the right upper hip 27, and the right thigh 28. These seven body injection areas correspond to the days of a week, allowing the user to rotate through the body parts, with one body part being assigned to a corresponding day of the week.

For example, on Monday, a self-injection may be performed in the body injection area of the left thigh 20. On Tuesday, a self-injection is the performed in the body injection area of the left hip 21. On Wednesday, the self-injection is performed in the body injection area of the left arm 22. On Thursday, the self-injection is then given in the body injection area of the abdomen 24. On Friday, the self-injection is performed in the body injection area of the right arm 26. On Saturday, the self-injection is given in the body injection area of the right hip 27. Finally, at the end of the one-week cycle, a self-injection is performed in the body injection area of the right thigh 28, on Sunday. The process may then be repeated the following week, with a week's time being given for healing of each body part.

It should be understood that the above was only a selected example, and that the sequence of days matching the body injection sites is entirely dependent upon the user, though once the sequence has been defined by the user, the tablet 10 should always have the same injection body area assigned to a particular day, thus allowing a one-week period being injections for each body part. Accordingly, by corresponding a body injection area with a particular day of the week, the user of the tablet 10 will easily remember, based upon the day of the week, where a self-injection is to be made. This eliminates repeating a self-injection in a particular body injection area during the week or week cycle. Thus, in a one-week cycle, each of the seven body injection areas 20, 21, 22, 24, 26, 27, and 28 will have been injected only once and only on its particular day of the week.

Each template in the tablet 10 includes a removable grid guide that is shaped to cover the particular body injection area. Additionally, each grid guide is divided into eight injection grids, numbered between one and eight. There is a unique numbering sequence to the eight injection grids, as shown in FIG. 3-9, as will be described in detail below. Generally, the unique numbering sequence of the injection grids is to ensure that there will be at least 5.08 centimeters, or a two-inch space, between injections.

Figure 3:
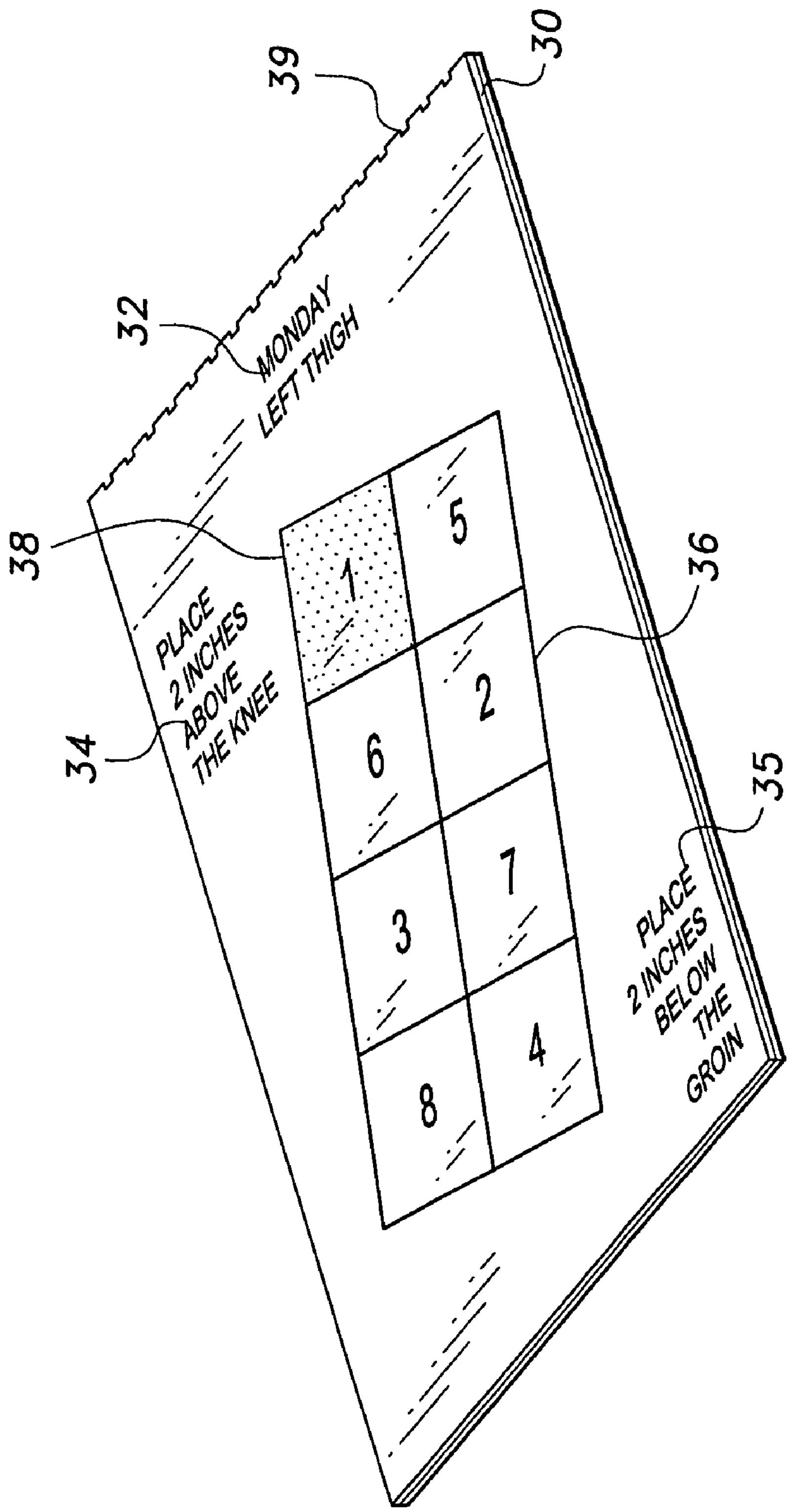
FIG. 3 is a perspective view of an individual first template with a first grid guide of the present self-injection guide tablet, for the left thigh injection area.

For example, on some of the guide grids, the injection grid number one is positioned catty-corner from injection grid number two, as injection grid number two is similarly catty-corner from injection grid number three (as shown in FIG. 3). Injection grid number three is catty-corner from injection grid number four. Similarly, injection grid number five is positioned catty-corner from injection grid number six, and injection grid number six is catty-corner from injection grid number seven. Further, injection grid number seven is catty-corner from injection grid number eight.

An alternative numbering sequence may also be assigned so as to ensure that no numbered injection grid is next to its sequentially numbered injection grid. This sequence also ensures that there is at least 5.08 centimeters, or at least two inches, between injection points. This sequence is used when the grid guide has the numbered injection grids in a row, as opposed to columns (as will be described in detail below).

In FIG. 3, a first template is illustrated, with the first template being configured for usage with the left thigh area 20. In the example of FIG. 3, area 20 has been assigned to Monday, and the following examples will be provided with each body part being assigned a sequential day from the first day of Monday, given in the example of FIG. 3. As noted above, the assignment of days to each body part is entirely dependent upon the user's preferences, and the assignments in FIGS. 3-10 are shown for exemplary purposes only.

The first template 30 includes indicia 32, shown here for exemplary purposes only as "Monday—Left Thigh", provided as a heading to guide the user. There are also instructions 34, 35 imprinted on the face of template 30 to indicate to the user where to place a first grid guide 36, once it is peeled from the first template 30. Thus, the user has the instructions 34, 35 readily available while using the first template 30 of the self-injection guide tablet 10.

The first grid guide 36 is preferably rectangular and includes eight injection grids, numbered one to eight, as described above. The numbering of the injection grids begins with an injection grid numbered one, preferably located in the top left corner, and indicated generally as 38. Each of the numbered injection grids identifies one injection area for the particular injection area.

The numbered injection grids are preferably formed in two columns, and the catty-corner numerical sequence described above is utilized to ensure that the injections are sequentially given for the selected body part at least 5.08 centimeters, or at least two inches, from the previous injection. A perforated edge 39 is shown at the top of template 30, near the spine 12, to permit removal of the first template 30 from the tablet 10.

When the user is ready to make the first injection, on Monday, the user will peel the first grid guide 36 from the first template 30 and place it 5.08 centimeters, or two inches, above the knee at the left thigh area 20, and two inches below the groin, as noted in the printed instructions 34, 35. Because the number one injection grid is placed at the knee, and the number four injection grid is positioned below the groin, the user can read the numbered injection grids during the performance of the self-injection.

Additionally, as the first grid guide 36 is peeled off, the number one grid 38 (shaded in FIG. 3) remains on the first template 30. As the first grid guide 36 is placed on the left thigh area 20, there will be an empty area, where the number one grid 38 is removed (by remaining fixed to template 30). The user will then perform the self-injection, within the open area of the vacated first grid. After self-injection, the first grid guide 36 is peeled off the left thigh area 20 and may be disposed of. Once the first grid guide 36 has been discarded, it obviously will not be used again in the first week, ensuring that there will not accidentally be an injection in the left thigh area 20. Once the user has gone through a full week of templates, on the following Monday, when injection is due in the left thigh area again, the number two space of the grid guide will be vacated, and on the third week, the number three space will be vacated, etc.

Figure 4:
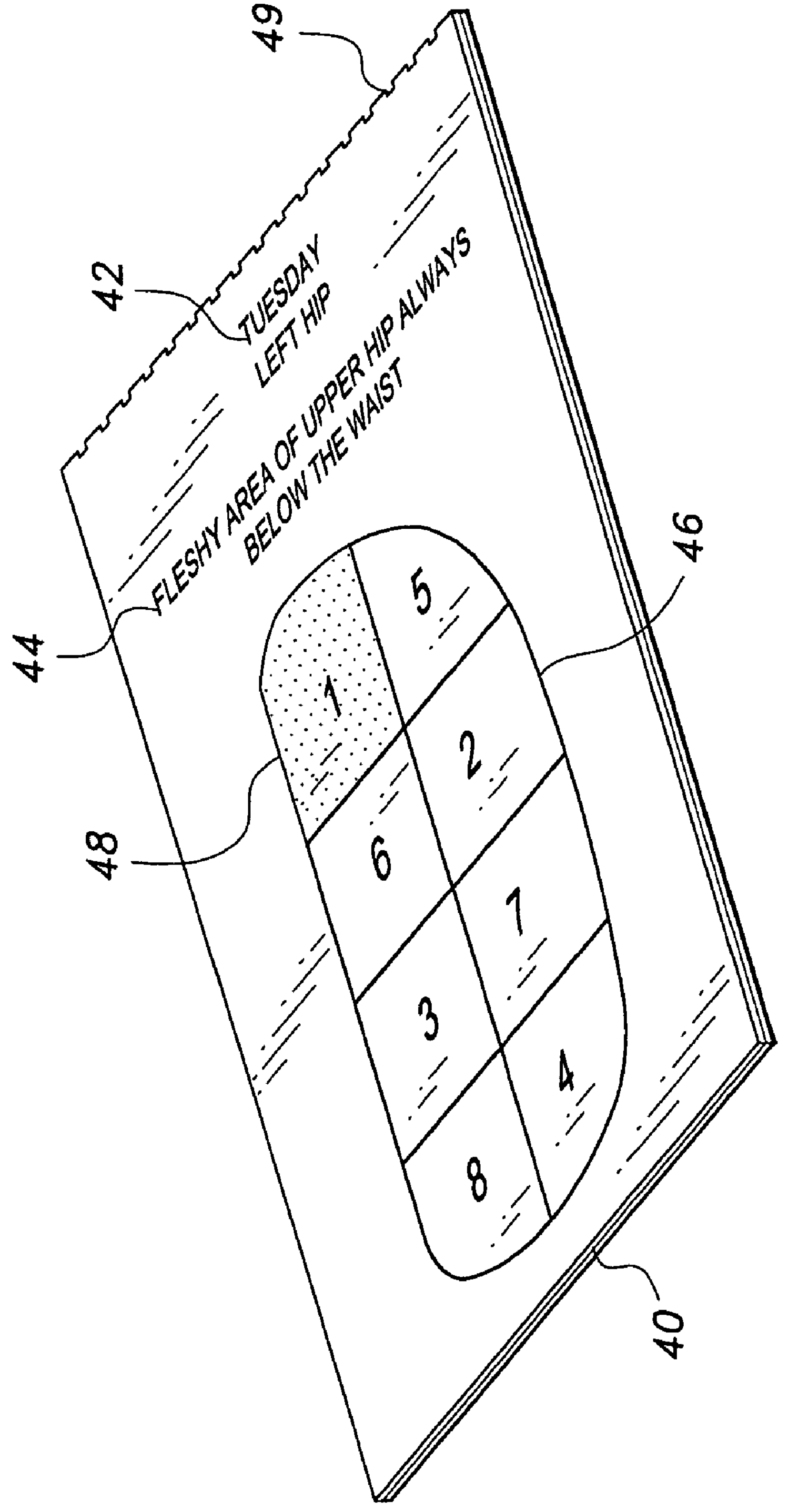
FIG. 4 is a perspective view of an individual second template with a second grid guide of the present self-injection guide tablet, for the fleshy area of the left hip.

FIG. 4 illustrates a second template 40. This second template 40 has indicia 42 formed thereon, forming a heading reading "Tuesday—Left Hip", in order to guide the user. As described above, there are instructions 44 for placement of a second grid guide 46 on the left hip area 21. The shape of the second grid guide 46 is similar to the configuration described above with regard to FIG. 3, with the injection grids numbered one, six, three, and eight in a first column (formed on the left on FIG. 4), and a second column, having a substantially half-elliptical shape, including injection grids numbered five, two, seven, and four. Thus, the catty-corner sequence is maintained to ensure that there is at least 5.08 centimeters, or at least two inches, between successive injections in the left hip area 21.

As this is the first week cycle, the number one injection grid, indicated generally as 48 and shown being shaded, will remain on the second template 40 when the second grid guide 46 is peeled off. The second grid guide 46 is placed on the fleshy area of the upper hip 21, below the waist, as indicated by instructions 44. When the injection is going to be preformed, the user injects into the empty injection grid area, where the number one injection grid 48 was removed. After injection, the second grid guide 46 is peeled off and discarded. Since, the grid guide 46 has been discarded, the user will not use the template 40 again in this first week cycle and will not inject in the left hip area 21 during this first week cycle. There is also a perforated edge 49 on the template 40, so the user may tear off the used template 40 from tablet 10, and discard it as well.

Figure 5:
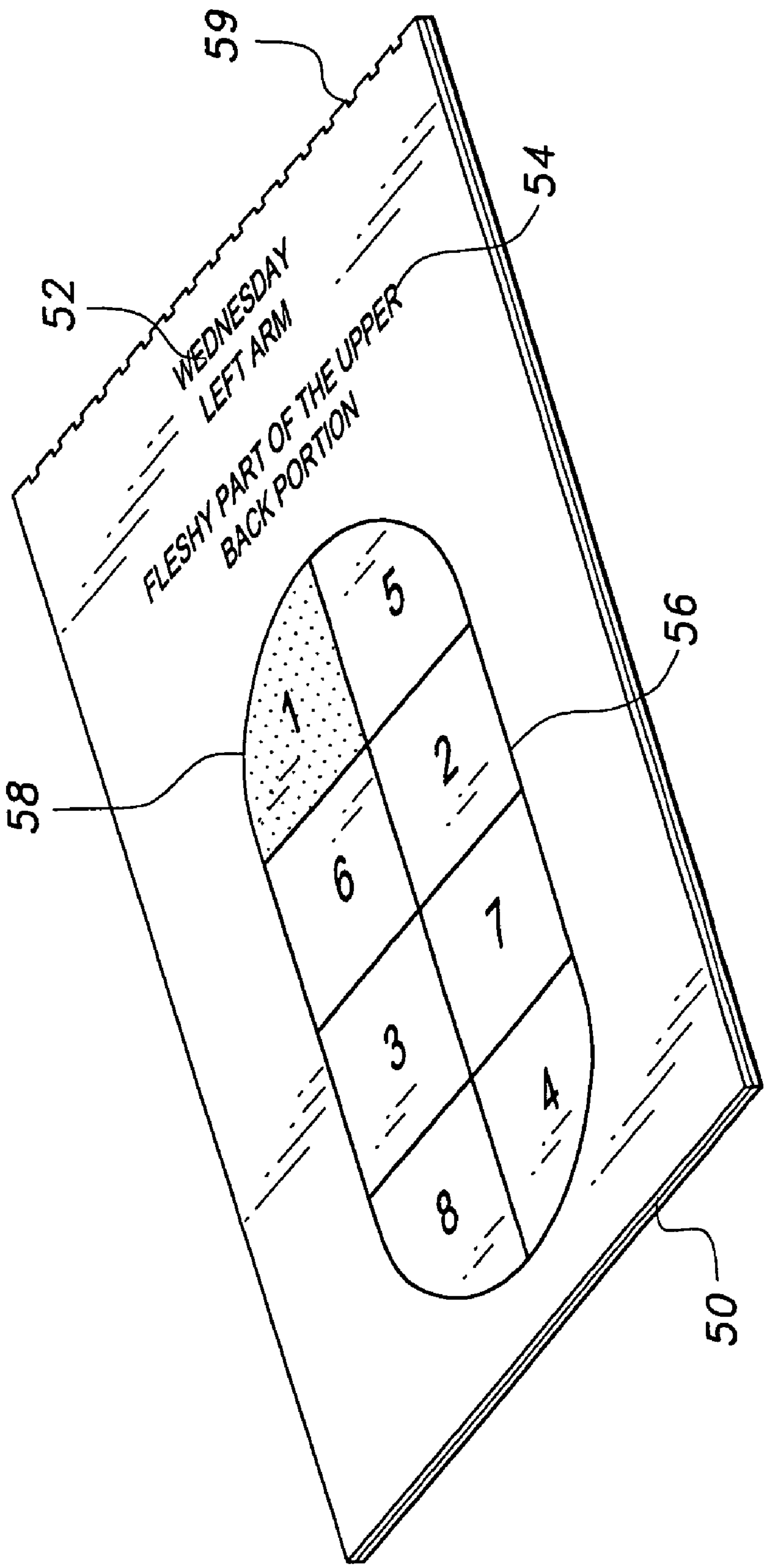
FIG. 5 is a perspective view of an individual third template with a third grid guide of the present self-injection guide tablet, for the left arm fleshy part of the upper back portion.

FIG. 5 shows a third template 50 of the tablet 10. This third template 50 has the indicia 52 formed thereon, reading "Wednesday—Left Arm", as well as instructions 54 for placement of a third grid guide 56 on the left arm area 22. The shape of the third grid guide 56 is substantially oval with the injection grids numbered one, six, three, and eight in a first column. The second column has the injection grids numbered five, two, seven, and four. As above, the catty-corner sequence is maintained to ensure that there is at least two inches from a previous injection grid any time an injection is given on a Wednesday into the left arm area 22.

As previously noted, this is Wednesday in the first week cycle. Since, it is still the first week cycle, the number one injection grid 58 is shaded, indicating that it will remain on the third template 50 when the third grid guide 56 is peeled off. As noted above, in the second week cycle, the number two grid will remain on the template as the grid guide 56 is removed from the template, and so on. The third grid guide 56 is placed on the fleshy area of the upper back portion of the left arm 22. The injection is preformed in the empty injection grid vacated by the number one injection grid 58. After the self-injection, the third grid guide 56 is peeled off the left arm 22 and discarded. A perforated edge 59 is formed near the spine 12 of the tablet 10, allowing the user to tear off the template 50 and discard it as well.

Figure 6:
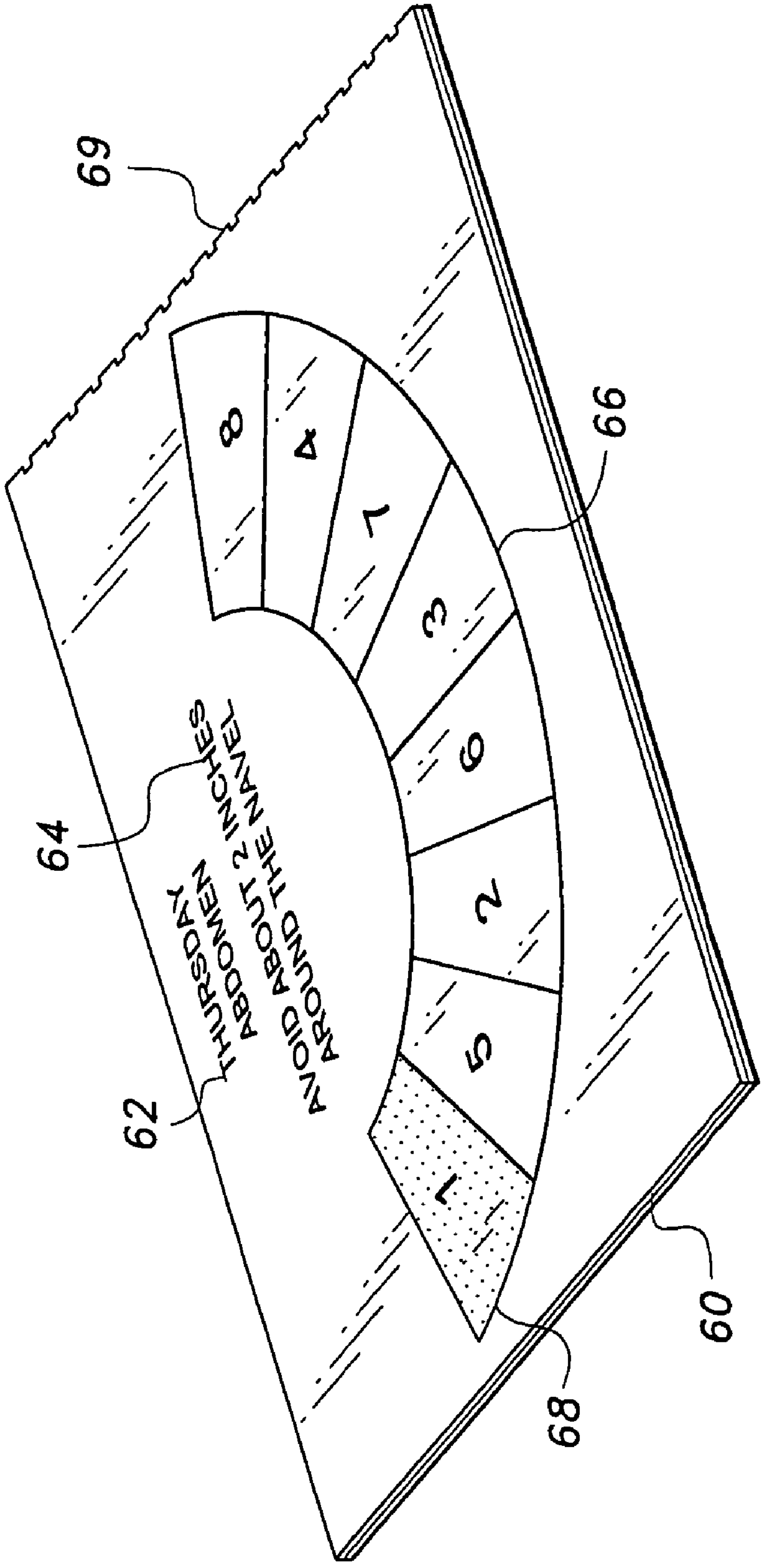
FIG. 6 is a perspective view of an individual fourth template with a fourth grid guide of the present self-injection guide tablet, for the abdomen.

FIG. 6 illustrates a fourth template 60 of the tablet 10. This fourth template 60 has indicia 62 formed thereon, reading "Thursday—Abdomen", as well as instructions 64 for placement of the fourth grid guide 66 on the abdomen injection area 24. The fourth grid guide 60 has an arch shape, with only one row of injection grids, numbered in a sequence of one, five, two, six, three, seven, four and eight. Fourth template 60 includes this arcuate configuration for grid guide 66 due to the unique contouring of the abdominal area. While the catty-corner sequence is not used on this fourth grid guide 66, this sequence still maintains at least 5.08 centimeters, or at least two inches, from a previous injection grid in the fourth grid guide 66, because each of the sequential numbered injection grids on the fourth grid guide 66 are approximately 5.08 centimeters, or two inches, apart.

As indicated previously, this is still the first-week cycle, so the number one injection grid 68 remains on the fourth template 60 when the fourth grid guide 66 is removed from the template 60. The fourth grid guide 66, with the number one injection grid 68 vacated, is placed on the fleshy area of the abdomen injection area 24. As the fourth grid guide 66 is placed on the abdomen injection area 24, the instructions 64 inform the user to avoid injection in the region about two inches around the navel. Once the self-injection is performed into the empty injection grid space vacated by the number one injection grid 68, the fourth grid guide 66 for the abdomen area 24 is peeled off and safely discarded. With the grid guide 66 being discarded, the user will not use the template 60 in this first week cycle again, and will not inject in the abdomen area 24 during the first week cycle. A perforated edge 69 near the spine 12 of the tablet allows the user to tear off the template 60 and discard it as well.

Figure 7:
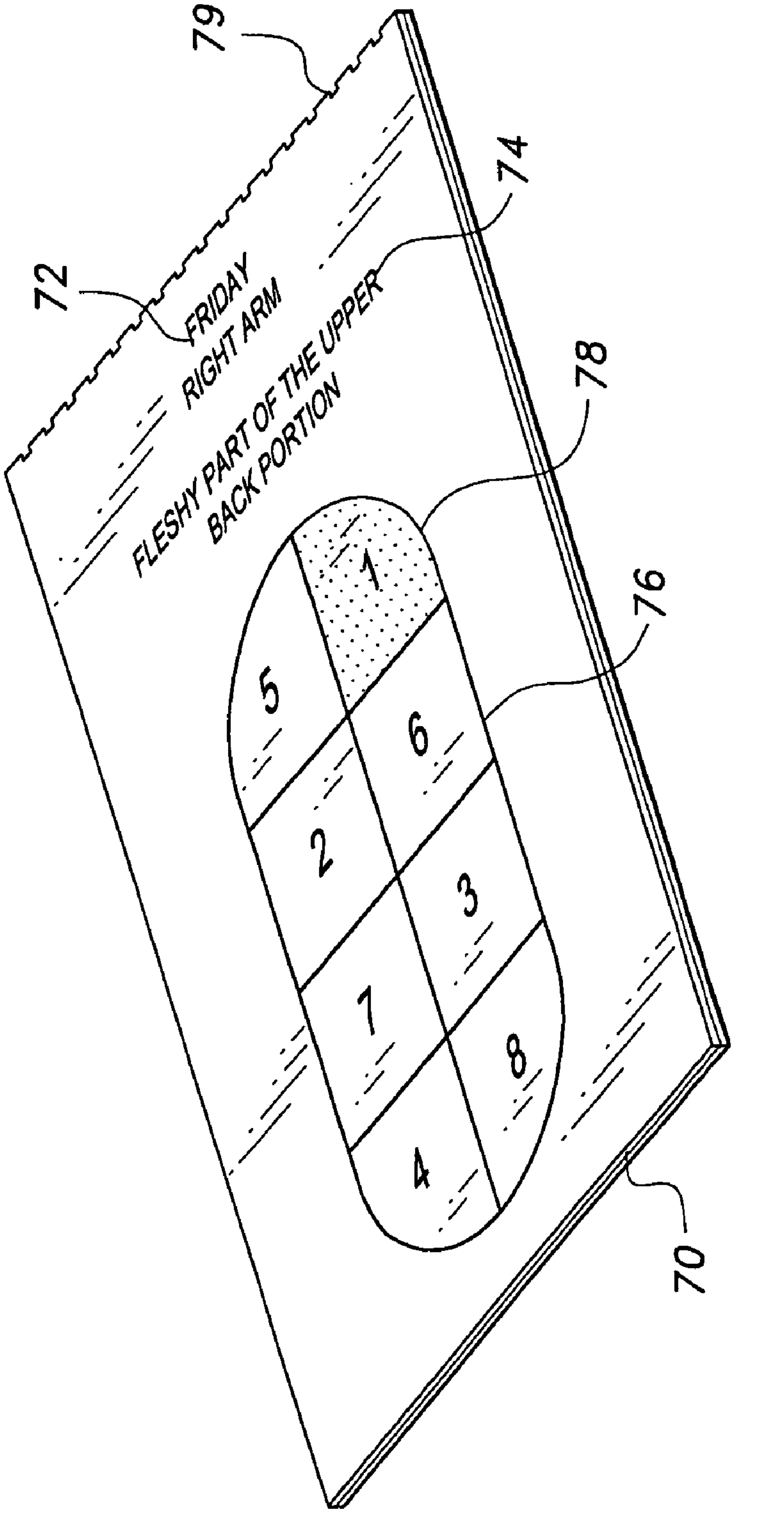
FIG. 7 is a perspective view of an individual fifth template with a fifth grid guide of the present self-injection guide tablet, for the right arm fleshy part of the upper back portion.

FIG. 7 shows a fifth template 70 of the tablet 10. Fifth template 70 includes indicia 72, forming a heading reading "Friday—Right Arm", as well as instructions 74 for placement of the fifth grid guide 76 on the right arm injection area 26. The shape of the fifth grid guide 76 is substantially oval to cover the right arm injection area 26. The fifth grid guide 76 has the injection grids numbered one, six, three, and eight in the right column. The other column has the injection grids numbered five, two, seven, and four.

As can be seen, the catty-corner sequencing of the numbers identifying the injection grids on the fifth grid guide 76 is used again. This catty-corner sequence ensures that no injection is made within a 5.08 centimeter, or a two inch, area from a previous injection in this right arm area 26. Additionally, the number one injection grid, indicated generally as 78, is in the opposite column, as opposed to the third grid guide 56 of FIG. 5, utilized with the left arm injection area 22. By switching or reversing the columns of the numbered injection grids, the user, when injecting in the same vacated injection grids in each arm, will inject in a symmetrical area, with respect to the other arm. For example, the injections made in the column with the number one injection grid will be on the outside of both the left arm 22 and right arm 26.

Again, this is still the first week cycle of self-injections. Since, it is the first week cycle of self-injections, the number one grid square 78, which is shown as being shaded, will remain on the fifth template 70 when the fifth grid guide 76 is peeled off and placed on the right arm injection area 26. This makes it simple for the user to perform injections, since the injection is made in the vacated spot left by the number one injection grid 78. After the self-injection, the fifth grid guide 76 is peeled off the right arm injection area 26 and conveniently discarded. With the grid guide 76 being discarded, the user will not use the template 70 again in this first week cycle, and will not inject in the right arm area 26 during the first week cycle. A perforated edge 79 near the spine 12 of the tablet 10 allows the user to tear off the template 70 and discard it.

Figure 8:
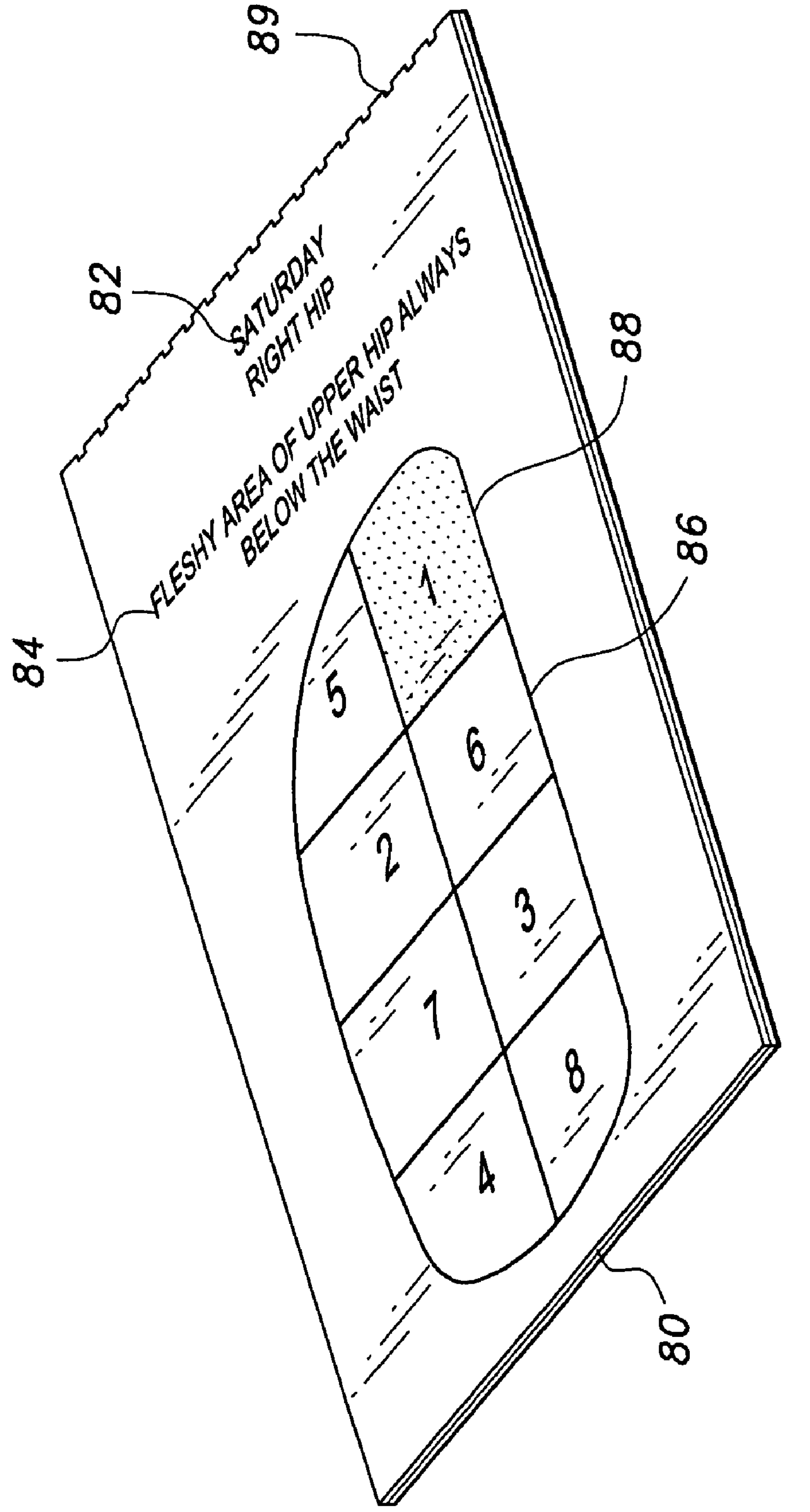
FIG. 8 is a perspective view of an individual sixth template with a sixth grid guide of the present self-injection guide tablet, for the fleshy area of the right hip.

With respect to FIG. 8, a sixth template 80 is illustrated. This sixth template 80 has indicia 82 formed thereon, forming a heading of "Saturday—Right Hip", as well as instructions 84 for placement of a sixth grid guide 86 on the right hip injection area 27. The shape of the sixth grid guide 86 is symmetrical with respect to the grid guide described above for the user's left hip injection area. In the right-hand column, a number one injection grid is indicated generally by numeral 88 and is shaded. This number one injection grid 88 is in a column with the injection grids numbered six, three, and eight. The second, half-elliptical column includes the injection grids numbered five, two, seven, and four. Thus, the catty-corner sequence described above is maintained.

Additionally, the number one injection grid 88 is in the opposite column compared to the second grid guide 46, shown in FIG. 4, utilized with the left hip injection area 21, as are all the numbered injection grids. By switching or reversing the columns of the numbered injection grids, the user, when injecting in the same vacated injection grids in each hip, will be in the same area of the body part; i.e., injection will be symmetrical about the center-line of the body. Since, this is still the first week cycle, the number one injection grid 88 will remain on the sixth template 80 as the sixth guide grid 86 is peeled and removed from the sixth template 80. The sixth guide grid 86 is then placed on the fleshy area of the upper right hip injection area 27, below the waist, as indicated by the instructions 84. The self-injection is performed in the open space left by the number one injection grid 88 and then the sixth grid guide 86 is peeled off and appropriately discarded. A perforated edge 89 is formed near the spine 12 of the tablet 10.

Figure 9:
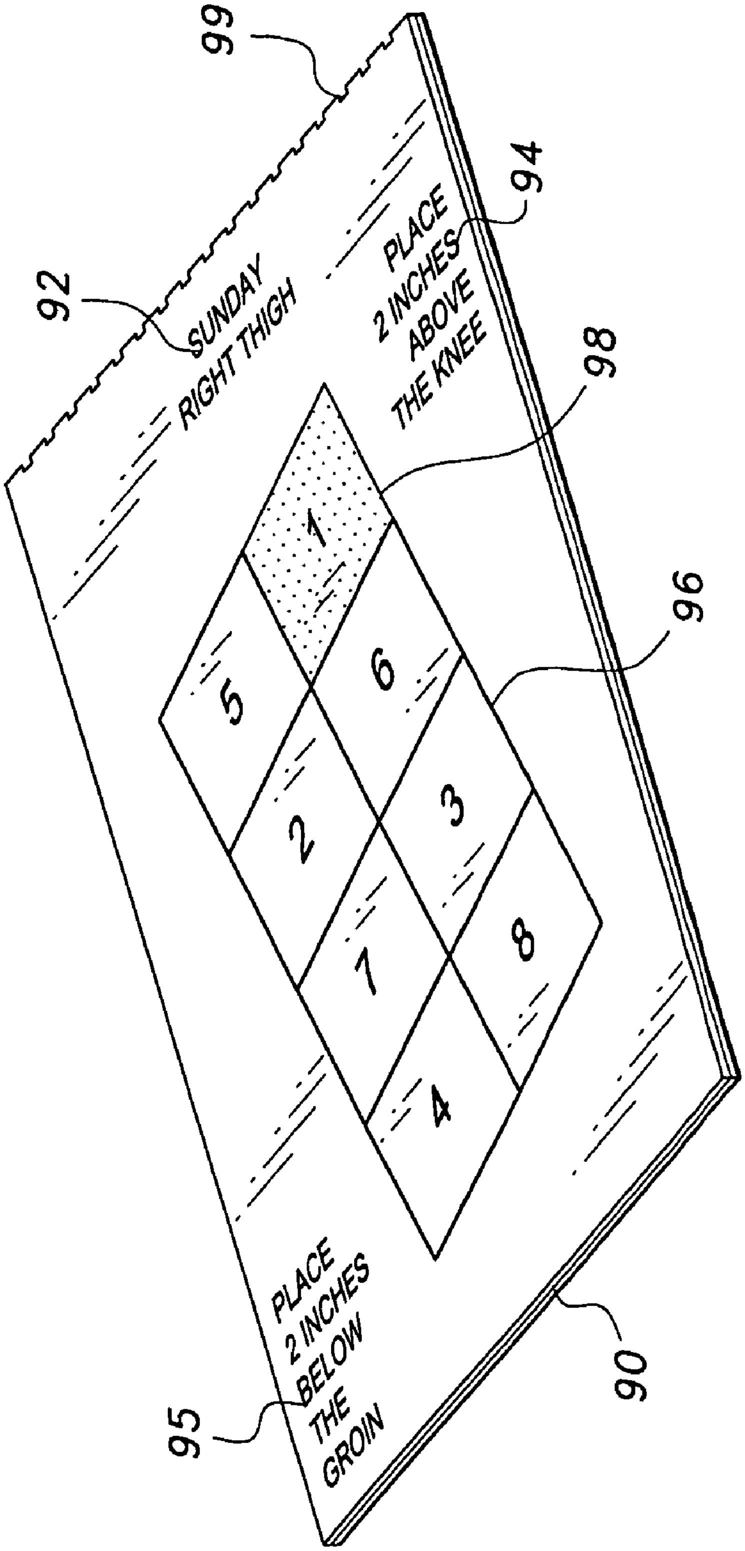
FIG. 9 is a perspective view of an individual seventh template with a seventh grid guide of the present self-injection guide tablet, for the right thigh injection area.

With respect to FIG. 9, on the seventh and final day of the first cycle week, a seventh template 90 is used for a self-injection into the right thigh injection area 28. The seventh template 90 includes indicia 92, forming a heading of "Sunday—Right Thigh", along with instructions 94, 95, indicating to the user where to place the seventh grid guide 96 once it is peeled from the seventh template 90. The seventh grid guide 90, for the right thigh injection area 28, is rectangular-shaped, similar to the first grid guide 36 for the left thigh injection area 20.

The number one injection grid 98, however, is in the opposite column from that of the first grid guide 36 (shown in FIG. 3), as are all the numbered injection grids. By switching or reversing the columns of the numbered injection grids, the user, when injecting in the same vacated injection grids in each thigh, will be in the same area of the body part, as described above.

As the instructions 94, 95 note, the seventh grid guide 96, after peeling from the seventh template 90, is placed two inches above the knee and two inches below the groin so that the user can read the numbers as he or she is performing a self-injection. As the seventh grid guide 96 is peeled off the seventh template 90 for the right thigh injection area 28, the number one injection grid 98 is shaded and remains on the template 90. The seventh guide grid 96 is then placed on the right thigh injection area 28, as indicated by the instructions 84. The self-injection is made in the open space left by the number one injection grid 98 and then the seventh grid guide 96 is peeled off and discarded. A perforated edge 99 is formed near the spine 12 of the tablet, allowing the user to tear off the template 90 and discard it as well. Thus, with the grid guide 96 being discarded, the user will not use the template 90 again in this first week cycle, and will not inject in the right thigh area 28 during the first week cycle again.

At this point, the week-long cycle has been completed, and the next injection is due on the next Monday, with the second week cycle to begin. The user will have used and discarded the seven grid guides 36, 46, 56, 66, 76, 86, and 96 from the seven daily templates 30, 40, 50, 60, 70, 80, and 90. The user will also have performed a self-injection in each of the seven injection areas 20, 21, 22, 24, 26, 27, and 28 utilizing the space vacated by the number one injection grids 38, 48, 58, 68, 78, 88, and 98. Thus, completing the first week cycle.

Now, on Monday of the second week cycle, the self-injection of seven injection areas 20, 21, 22, 24, 26, 27, and 28 begins again. However, in the second week cycle, each of the seven grid guides 36, 46, 56, 66, 76, 86, and 96 of each of the seven templates 30, 40, 50, 60, 70, 80, and 90 in the tablet 10 will have all seven of the number two injection grids shaded when the user makes a self-injection. The number one injection grids 38, 48, 58, 68, 78, 88, and 98 are not shaded and are part of the respective grid guide 36, 46, 56, 66, 76, 86, and 96 when peeled and placed on the respective injection areas 20, 21, 22, 24, 26, 27, and 28. Thus, the user can easily complete their daily injections for the second week.

This injection cycle repeats over an eight-week cycle that corresponds to the eight numbered injection grids in each of the seven guide grids 36, 46, 56, 66, 76, 86, and 96. Thus, the tablet 10 will be completed after approximately a two-month period. Preferably, each tablet 10 is manufactured to include eight sets of the seven templates 30, 40, 50, 60, 70, 80, and 90 in the tablet 10.

It should also be noted that the perforations 39, 49, 59, 69, 79, 89, and 99 added to each of the templates in the tablet 10 allow the user to remove an entire template or more, if necessary. Such removal could be utilized when the user is on a trip and only needs to take a few days worth of templates for self-injections, rather than bringing the entire tablet 10. Alternatively, the user may want to remove a respective template from the tablet 10 after using and discarding the respective grid guide.

The use of an adhesive backing, such as found on adhesive bandages, does not necessarily have to cover the entire back of the template, it is only required to have enough adhesive surface area to hold a grid guide on a template, and to ensure the grid guide adheres to the body injection area long enough for the self-injection (and to be readily removable without much discomfort to the user).

Additionally, the tablet can be modified for those individuals who require more than one injection per day or even for those who require between one and several injections per week. Some medications require varied injections times. For example, Rebif® requires injection three times per week, whereas Humira® requires injection only every other week. Tablet 10 may be customized to accommodate such irregular injection schedules. With respect to the numbering on the injection grids, the use of numbers one through eight is common in the medical field to identify an injection area. However, letters or other indicia could be alternatively used to guide the individual making self-injections.

Furthermore, general instructions could be printed on one or both of the covers 14, 16. In use, the user should wash and dry his or her hands prior to peeling the grid guide from the template. The user should then place the grid guide on the area indicated (e.g., right thigh, right hip, etc.), with the adhesive backing holding the guide in place. The user should clean the skin in the open injection grid area with an alcohol pad, or with any other suitable sanitizer, and allow the skin to dry. The self-injection is given in the open injection grid, and then gentle pressure is applied with a cotton ball or gauze to dry the open injection grid area. Finally, the entire grid guide is peeled and discarded. The user should avoid injection in areas with stretch marks, bruises, tattoos, scars, lesions, swelling, lumps, redness, or warts.

It is to be understood that the present invention is not limited to the embodiment described above, but encompasses any and all embodiments within the scope of the following claims.

I claim:

1. A self-injection guide tablet, comprising:

at least one template for administering subcutaneous self-injections;

a removable guide grid releasably mounted on the at least one template, the removable guide grid including a plurality of injection grids; and indicia formed on the at least one template, the indicia including instructional material for instructing a user during self-injection, sequential indicia being formed on each of the injection grids to indicate to the user a particular injection grid to be removed from the removable guide grid, removal of the particular injection grid forming an injection area.

2. The self-injection guide tablet as recited in claim 1, wherein the indicia formed on the at least one template includes a day of the week and a location on the individual for the subcutaneous self-injection.

3. The self-injection guide tablet as recited in claim 2, wherein said at least one template comprises at least one set of seven templates, each of the seven templates corresponding to a separate body part and a separate day of the week.

4. The self-injection guide tablet as recited in claim 3, wherein said at least one template comprises at least two sets of seven templates, each set corresponding to a week of self-injections.

5. The self-injection guide tablet as recited in claim 4, wherein said plurality of injection grids includes an injection grid corresponding to each week of self-injections.

6. The self-injection guide tablet as recited in claim 5, wherein each said injection grid corresponding to successive weeks of self-injection are positioned at least two inches from one another.

7. The self-injection guide tablet as recited in claim 1, wherein the particular injection grid removed from the removable guide grid is fixed to the at least one template.

8. The self-injection guide tablet as recited in claim 1, further comprising means for releasably attaching said removable guide grid to the at least one template and to the user's skin.

9. The self-injection guide tablet as recited in claim 8, wherein said means for releasably securing said removable guide grid to the at least one template and to the user's skin comprises an adhesive layer formed on a rear surface of said removable guide grid.

10. The self-injection guide tablet as recited in claim 9, further comprising upper and lower covers, said at least one template being sandwiched between the upper and lower covers.

11. The self-injection guide tablet as recited in claim 10, further comprising a spine, the upper cover, the lower cover and the at least one template being joined to the spine along respective upper edges thereof.

12. The self-injection guide tablet as recited in claim 11, wherein the upper edge of said at least one template is releasably secured to the spine by perforations.

13. A self-injection guide tablet, comprising:

at least one template for administering subcutaneous self-injections, the at least one template having at least one set of seven templates, each of the seven templates corresponding to a separate body part and a separate day of the week;

a removable guide grid releasably mounted on the at least one template, the removable guide grid including a plurality of injection grids; and indicia formed on the at least one template, the indicia including instructional material for instructing a user during self-injection and including a day of the week and a location on the individual for the subcutaneous self-injection, sequential indicia being formed on each of the injection grids to indicate to the user a particular injection grid to be removed from the removable guide grid, removal of the particular injection grid forming an injection area.

14. The self-injection guide tablet as recited in claim 13, wherein the particular injection grid removed from the removable guide grid is fixed to the at least one template.

15. The self-injection guide tablet as recited in claim 13, further comprising means for releasably securing said removable guide grid to the at least one template and to the user's skin.

16. The self-injection guide tablet as recited in claim 15, wherein said means for releasably securing said removable guide grid to the at least one template and to the user's skin comprises an adhesive layer formed on a rear surface of said removable guide grid.

17. The self-injection guide tablet as recited in claim 16, further comprising upper and lower covers, said at least one template being sandwiched between the upper and lower covers.

18. The self-injection guide tablet as recited in claim 17, further comprising a spine, the upper cover, the lower cover and the at least one template being joined to the spine along respective upper edges thereof, the upper edge of said at least one template being releasably secured to the spine by perforations.

19. The self-injection guide tablet as recited in claim 18, wherein said at least one template comprises at least two sets of seven templates, each of the sets corresponding to a week of self-injections.

20. The self-injection guide tablet as recited in claim 19, wherein said plurality of injection grids includes an injection grid corresponding to each week of self-injections, each said injection grid corresponding to successive weeks of self-injection being positioned at least two inches from one another.

* * * * *